United States Patent
Nyfeler et al.

(10) Patent No.: US 11,103,036 B2
(45) Date of Patent: Aug. 31, 2021

(54) METHOD FOR RENDERING A GEMSTONE TRACEABLE

(71) Applicant: Gübelin Gem Lab Ltd., Lucerne (CH)

(72) Inventors: Daniel Nyfeler, Rütschelen (CH); Klemens Link, Malters (CH)

(73) Assignee: GÜBELIN GEM LAB LTD., Lucerne (CH)

( * ) Notice: Subject to any disclaimer, the term of this patent is extended or adjusted under 35 U.S.C. 154(b) by 111 days.

(21) Appl. No.: 16/489,729

(22) PCT Filed: Mar. 2, 2018

(86) PCT No.: PCT/EP2018/055212
§ 371 (c)(1),
(2) Date: Aug. 29, 2019

(87) PCT Pub. No.: WO2018/158444
PCT Pub. Date: Sep. 7, 2018

(65) Prior Publication Data
US 2019/0365063 A1 Dec. 5, 2019

(30) Foreign Application Priority Data
Mar. 2, 2017 (CH) .................................. 00258/17

(51) Int. Cl.
*A44C 27/00* (2006.01)
*A44C 17/00* (2006.01)

(52) U.S. Cl.
CPC .......... *A44C 17/007* (2013.01); *A44C 27/005* (2013.01)

(58) Field of Classification Search
CPC .............................. A44C 17/007; A44C 27/005
See application file for complete search history.

(56) References Cited

U.S. PATENT DOCUMENTS

| 6,391,215 B1 * | 5/2002 | Smith | ...................... B44B 7/00 |
| | | | 204/192.1 |
| 7,398,658 B2 * | 7/2008 | Benderly | ................. B41M 5/26 |
| | | | 216/28 |

(Continued)

FOREIGN PATENT DOCUMENTS

| GB | 2 387 437 | 10/2003 |
| WO | 02/10091 | 2/2002 |

(Continued)

OTHER PUBLICATIONS

English translation of International Preliminary Report on Patentability dated Sep. 3, 2019 (Sep. 3, 2019), Application No. PCT/EP2018/055212, 9 pages.

(Continued)

*Primary Examiner* — Jack W Lavinder
(74) *Attorney, Agent, or Firm* — Rankin, Hill & Clark LLP

(57) ABSTRACT

A method for rendering a gemstone traceable, includes the steps: providing an invisible marker, wherein the marker is unambiguously identifiable, fastening the marker in a placement location of the gemstone, and acquiring marking information that includes that this unambiguously identifiable marker is fastened to this gemstone. The marker can be transported to the placement location in a manner in which it is suspended in a carrier fluid. An additive, for example a primer or a starting material for a surface coating of at least a part surface of the placement location, can be added to the carrier fluid.

15 Claims, 2 Drawing Sheets

(56) References Cited

U.S. PATENT DOCUMENTS

| | | | |
|---|---|---|---|
| 9,360,589 B1* | 6/2016 | Meinhold | B82Y 15/00 |
| 2001/0032831 A1* | 10/2001 | Benderly | H01S 3/106 |
| | | | 219/121.68 |
| 2005/0019556 A1 | 1/2005 | Freeman et al. | |
| 2008/0225266 A1* | 9/2008 | Van De Velde | G01N 33/381 |
| | | | 356/30 |
| 2009/0286250 A1 | 11/2009 | Hayward et al. | |
| 2014/0312248 A1* | 10/2014 | Beck | G01N 21/65 |
| | | | 250/459.1 |
| 2015/0107475 A1* | 4/2015 | Jung | B42D 25/378 |
| | | | 101/483 |

FOREIGN PATENT DOCUMENTS

| | | |
|---|---|---|
| WO | 02/086052 | 10/2002 |
| WO | 2006/053435 | 5/2006 |
| WO | 2013/143014 | 10/2013 |

OTHER PUBLICATIONS

Switzerland Search Report dated Aug. 15, 2017, Application No. CH 2582017, 3 pages.

* cited by examiner

METHOD FOR RENDERING A GEMSTONE TRACEABLE

BACKGROUND OF THE INVENTION

Field of the Invention

The invention relates to the field of methods for rendering gemstones traceable. The rendering traceable permits a tracing of a gemstone. The tracing of gemstones is an important piece of information for the purchaser of gemstones.

Description of Related Art

By way of the tracing, one can determine for example the origin of a gemstone. Information concerning specific mines and/or geographic regions is possible in this manner. Information on an origin from official mining and/or marketing channels is also possible. A processing of the gemstone for example can likewise become transparent due to the tracing. Depending on the application of the method for tracing, by way of the tracing one can therefore discover from where a gemstone originates, through which hands it has gone and/or when and where it has been processed.

By way of the tracing, one can prevent stolen, counterfeit and/or smuggled gemstones from being traded as normal gemstones. Gemstones from illegal mines, from mines with exploitative environments and/or from mines in war zones can also be recognised.

The tracing of gemstones can hence lessen or remedy the negative aspects of trading gemstones. However, the tracing can also increase the value of gemstones due to the verifiability of their origin. The tracing of gemstones is of increasing importance in globalised trade. It is for this reason that a rendering traceable of a gemstone is of interest to many parties.

Various such methods for tracing gemstones are known for example from WO0210091A2. The state of the art of methods for the rendering-traceable which is described therein includes (laser) engraving and etching methods for marking gemstones. This, however, compromises and/or damages the gemstone. The method which is described in WO0210091A2 includes a removable envelope of the gemstone, in particular with a polymer casing. The casing can include unambiguously identifiable characteristics, for instance by way of a certain chemical composition of the casing and/or by way of markings on the casing in different ways and manners (for example, barcodes, holograms, matrices, fluorescing colour particles, etc.).

The disadvantage of the known methods is the fact that a gemstone is compromised or even damaged on rendering it traceable. Or the gemstone is rendered traceable by a method that permits a removal of the identification possibility (for example of the polymer casing). A manipulation of the tracing is possible due to the removal of the identification possibility. Such a method is not very secure and can be unreliable.

Another disadvantage of the known methods is the fact that by way of this, the gemstones can be compromised in their optical quality. Said differently, known methods for rendering traceable cause changes on a gemstone which are visible to the human eye. For example, barcodes or envelopes are attached to the gemstone. Changes which are visible to the naked eye however reduce the value of a gemstone, particularly if this is already finished in its processing.

A further disadvantage of the known methods for rendering traceable is the fact that the traceability of a gemstone is compromised or even impossible after a processing of the gemstone. For example, an engraved or etched marking can be partly or completely damaged or even removed after a grinding or cutting of the gemstone. An encasing of the gemstone can likewise become partly or completely damaged or even removed on firing, irradiating, grinding, cutting, oiling, greasing, paraffining and/or waxing. In the case of known methods for example, depending on the method, a gemstone can only be poorly traced or even not at all in the state of being completed in its processing (with or without a holder).

SUMMARY OF THE INVENTION

It is therefore the object of the invention to create a method for rendering gemstones traceable, which at least partly remedies at least one of the aforementioned disadvantages.

The method according to the invention for rendering a gemstone traceable includes the steps:

providing an invisible marker, wherein the marker is unambiguously identifiable, fastening the marker in a placement location of the gemstone, and acquiring marker information which includes that this unambiguously identifiable marker is fastened to this gemstone.

A gemstone is sometimes also called a precious stone. A gemstone, for example, is an emerald, a diamond, a ruby, a sapphire, a corundum, an agate, a beryl, a malachite, a tourmaline or a topaz. A precious stone as well as a semi-precious stone are also included by the term gemstone. A gemstone can be a mineral, a stone, a glass melt or a substance of organic origin (such as, for example, amber, bituminous lignite or a fossil or a fossil piece). Pearls, mother of pearl and corals are also counted as being gemstones.

In particular, the gemstone is of a natural origin.

What is meant by natural origin is that the gemstone is not artificially manufactured. In other words, a gemstone of a natural origin has arisen and can be found in nature. For example, a gemstone of a natural origin is mined in mines. The gemstone is alternatively manufactured synthetically.

In particular, the gemstone is a beryl and in particular an emerald, thus a green beryl.

A marker is a physical object which extends spatially in three dimensions. An invisible marker is not visible to the naked human eye. In other words, the marker is denoted as being invisible if a human cannot see the marker without any aid. The marker can be invisible for example due to the size, the refractive index, density, transparency and/or reflection.

In particular, the marker is also not visible with optical instruments.

What is meant by optical instruments are instruments that achieve an image magnification exclusively in an optical manner, thus by using optical lenses. Optical instruments, for example, are glasses, magnifying glasses or light microscopes, thus light-optical devices and instruments. In contrast, electron microscopes or scanning probe microscopes are explicitly not optical instruments within the framework of this application.

A marker includes a characterising characteristic that permits an unambiguous identification of the marker. The marker is unambiguously identifiable if it can be clearly ascertained that it is the case of precisely one specific marker. The characterising characteristic of the marker can be an individual characteristic or consist of a combination of specific characteristics.

For example, a marker can include DNA, radioactively radiating constituents, isotopes, trace elements, metals of rare earths, be polarised, be electrically charged, be magnetised, have a certain quantum state, include fluorescing and/or phosphorescing constituents and/or have a specific chemical signature and be unambiguously identifiable on the basis of one or more of these characteristics.

In particular, the characterising characteristic can include the marker including an isotope.

In particular, the characterising characteristic can include the marker including several isotopes in a specific quantity ratio.

In particular, the characterising characteristic can include the marker including a metal of the rare earths (REE).

The characterising characteristic of the marker can include for example at least 50 different values or identities, which can be clearly differentiated from one another. For example, the characterising characteristic of the marker can include at least 100 different values. In particular, the characterising characteristic of the marker can include at least 500 different values. What is meant by this is that an identification and differentiation of at least 50 or 100 or 500 markers of the same type (i.e. with the same characterising characteristic) is possible by way of the marker. A positive or a negative charge alone is not therefore sufficient in order to unambiguously identify a marker in the context of the example which is described in this paragraph.

A marker for example permits a marking and identification of an object, to which the marker is assigned. An object to which a marker is assigned can be recognised and traced in this manner. A gemstone can be rendered traceable by a marker.

Herein, one can use a single marker, or however a plurality of identical markers which cannot be differentiated from one another (thus markers of the same variety, which is to say markers which have the same characterising characteristic with the same value). When one speaks of a marker in the application, this implicitly also means a plurality of markers of the same variety inasmuch as this should makes sense.

A plurality of markers of the same variety can simplify and/or improve the traceability of the object, for example by way of a marker of several markers on an object being able to be found more quickly than an individual marker on the object. For example, a plurality of markers on an object can provide a stronger measurement signal of a measuring method of the characterising characteristic of the marker than an individual marker on the object. The traceability can be improved by a plurality of markers of the same variety, since a removal of or damage to an individual marker that is fastened to the object can be compensated by the presence of other markers of the same variety on the object.

A placement location denotes a location on the gemstone that is arranged in the inside of the gemstone and that has enough space for a marker. In other words, the placement location is a spatial volume at a position in the gemstone that does not lie on the outer surface of the gemstone. The placement location includes at least a spatial volume of the size of the marker. The placement location for example is a crack, a micro-crack, a fissure, a gap, a scratch, a deepening, a defect location, a defect, a bubble, a cavity, a crystal lattice defect and/or a passage inherent of the crystal structure or the crystal growth, such as, e.g., twin surfaces of sub-grain boundaries.

In particular, the placement location is a crack.

A crack in a gemstone is a narrow opening in the gemstone extending from the outer surface of the gemstone into the inside of the gemstone. Herein, a depth of the crack is larger than a width of a crack by at least a factor of five, in particular by a factor of 10. In particular, the crack is deeper than it is wide by a factor of 50. A length of the crack can vary, but is always larger than the width of the crack. The length and the width of the crack run for example along the surface of the gemstone. A micro-crack is also a crack.

In particular, the placement location is formed naturally in the gemstone.

This means that, for example, naturally arisen defects of the gemstone are used as a placement location. A gemstone can be rendered traceable whilst using its natural characteristics in this manner, without the gemstone being subjected to damage, being manipulated in its basic substance, being structurally changed, or being optically changed and/or being reduced in its financial value, by it being rendered traceable.

Additionally or alternatively, a placement location can also be created artificially on the gemstone. For example, a placement location can arise on mining a natural gemstone, for instance with an explosion and/or other influences such as pressure change, mechanical loading and unloading and/or friction during the mining and/or the transport.

What is meant by fastening in the placement location is that the marker is arranged in the placement location in a manner in which it is positionally fixed relative to the gemstone. The marker is therefore immovably fixed in the placement location.

In particular, the marker is releasably fastened in the placement location.

After the fastening, the marker can therefore, for example, be released from the placement location again. Depending on the type of fastening, the release of the marker from the placement location can depend on a certain technology and/or certain conditions or constraints. For example, a specific fastening substance can only be dissolved by a specific solvent.

In particular, the marker is insolubly fastened in the placement location.

What is meant by acquiring marker information is that at least certain information, specifically which unambiguously identifiable marker has been fastened in the placement location of which gemstone, is provided in a retrievable manner. The marking information can also include further information, for example the point in time, location or coordinates and/or further information (such as names of natural or legal persons, observations and number values) concerning the mining, marking, processing, transport, sale of the gemstone and/or of a completely different nature.

By way of the method according to the invention, it is possible to render a gemstone traceable. The marker is not visible to the naked human eye, and by way of this the gemstone is not optically compromised by the rendering traceable. The invisible marker can remain fastened to the gemstone for an unlimited amount of time in this manner, without changing its appearance or this becoming compromised. A change or even compromising of the appearance of the gemstone could reduce its value. Conversely, the value of a traceable gemstone can increase compared to a non-traceable gemstone, above all if the rendering traceable does not compromise or change its appearance.

The marker is fastened in a placement location in the gemstone, by which means it is arranged in the inside of the gemstone. By way of this positioning in the placement location, the marker is protected from processing steps and/or attempts at manipulation.

Due to the invisibility of the marker to the naked eye and, made possible by way of this, the fact that it can remain in the placement location of the gemstone for an unlimited period of time without being bothersome, the gemstone can always be unambiguously identified again and again from the point in time of the fastening of the marker. An intermediate removal of the identification feature—thus finally of the marker—for a processing and/or for a final use (for example in a holder as a piece of jewellery) as with the state of the art, is done away with. Herein, the intermediate removal can be carried out deliberately as with the encasing in the aforementioned state of the art. Or the intermediate removal is effected in any case, for example on grinding the gemstone and the removal of an engraving or etching of the surface of the gemstone which results from this. The remaining of the marker in the placement location and, by way of this, in the gemstone, renders the method reliable, safe and resistant to manipulation.

Analogously, it is also the case that this method for rendering traceable is reliable, safe and/or resistant to manipulation for the positioning of the marker in the placement location and the resulting protection from processing steps and/or manipulation.

In it is indeed by way of the interaction of these two features (specifically the invisible marker and the fastening of the marker in the placement location) that the described method for rendering traceable is particularly secure. The permanent remaining of the marker in the gemstone—made possible by the invisible marker which can be fastened on the gemstone for an unlimited period of time without optical disadvantages—and the protection of the marker from manipulation and/or processing steps—made possible by the fastening of the marker in the placement location—make the method for rendering traceable particularly reliable, secure and/or resistant to manipulation. Without the invisibility of the marker, the marker should not remain on the gemstone for an unlimited amount of time and should therefore also not be brought into the protected placement location. And without the mechanical protection of the placement location, the marker would be fastened to the gemstone in a less secure manner and less resistant to manipulation.

For example, the described method for rendering a gemstone traceable can be applied to a gemstone in the different stages of its processing. The method can be applied just as well to a raw gemstone as to a partly processed gemstone and/or to a gemstone which has completed its processing. This is advantageous, since a gemstone can be rendered traceable independently of its degree of processing.

A multiple use of the method with markers which are different from one another and thus distinguishable markers is also possible. For example, various trade routes and/or processing stages can be rendered traceable by way of this.

In particular, the gemstone is encompassed by a piece of jewellery before the fastening of the marker in the placement location of the gemstone.

In other words, the gemstone can be rendered traceable by way of the described method, even if the gemstone is already arranged in a piece of jewellery. Herein, the piece of jewellery can be formed and/or processed only partly or however in an already completed manner. The described method can therefore also be applied to gemstones in partly-finished or finished pieces of jewellery.

Due to rendering the gemstone traceable, the piece of jewellery which encompasses this gemstone can likewise be rendered traceable, inasmuch as the piece of jewellery encompasses the gemstone on rendering traceable. The marking information can also include information concerning the piece of jewellery. In this manner, a piece of jewellery or also only parts of a piece of jewellery can be rendered traceable. An origin of a gemstone from a piece of jewellery can also be derived. Stolen gemstones and/or pieces of jewellery can be identified in this manner. The rendering traceable can also make a piece of jewellery somewhat more forgery-proof.

Optionally, the marker is transported to the placement location in a manner in which it is suspended in a carrier fluid, in order to fasten the marker in the placement location of the gemstone.

A suspending of the marker in a carrier fluid permits a simple and efficient transport to the placement location. Suspended means that the marker is essentially enclosed by the carrier fluid. In the case of several markers, the suspended markers are distributed in the carrier fluid. The marker suspended in the carrier fluid can easily be brought into the placement location. The carrier fluid can also help to bring several markers into one or more placement locations in a uniform distribution.

In particular, the carrier fluid is fluid at room temperature.

In this manner, the marker can be simply suspended in the carrier fluid at room temperature. The transport of the marker to the placement location can also be effected at room temperature, which entails a low technical effort.

In particular, the carrier fluid is in a solid aggregate state at room temperature. For example, the carrier fluid is present in powder form at room temperature.

The carrier fluid does not become fluid, for example, until at a temperature of at least 80 degrees Celsius. In particular, the carrier fluid does not become fluid until at a temperature of at least 150 degrees Celsius. In particular; the carrier fluid does not become fluid until at a temperature of at least 300 degrees Celsius.

An example for a carrier fluid with a solid aggregate state at room temperature is glass, and in particular lead glass. Lead glass is glass with a relatively low melting temperature and with different compositions, to which lead is added. The lead in the glass increases the light refraction and approximates that of a gemstone, for example that of a ruby.

Optionally, the carrier fluid includes a flow means for a gemstone. In particular, the carrier fluid is a flow means for a gemstone.

A fluid means for a gemstone permits the gemstone to be at least partly solubilised or dissolved at a relatively low temperature. Expressed differently, the melting temperature of the gemstone is reduced by the flow means. Another description for the flow means is flux means. Thus with the application of flow means, the melting point of a gemstone for example of a corundum (such as a ruby or sapphire) is lowered, so that this gemstone melts at lower temperatures than without flow means and in particularly partially melts at lower temperatures than without flow means.

Flow means can be used with the so-called firing or heating of a gemstone, in order to reduce and/or remedy imperfections of the gemstone more simply and rapidly than would be effected on firing or heating without flow means. Imperfections of the gemstone can be potential placement locations, thus for example a crack, a micro-crack, a fissure, a gap, a scratch, a deepening, a defect location, a defect, a bubble, a cavity, a crystal lattice defect and/or a passage which is inherent of the crystal structure or the crystal growth, such as e.g. twin surfaces or sub-grain boundaries. By way of the flow means, a part melt of the gemstone (thus a melt which is caused by way of a partial melting of the gemstone) can get to locations with the imperfections and defects or remedy these, to a better extent than is the case without flow means.

On firing, the flow means is fluid and can make up at least a part of the carrier fluid, in which the marker is suspended, in order to be transported to the placement location.

Optionally, the carrier fluid includes a melt including a flow means for a gemstone as well as a part-melt of the gemstone. In particular, the carrier fluid is a melt including a flow means for a gemstone as well as a part-melt of the gemstone.

A melt which includes molten gemstone (in particular coming from a partial melting of the gemstone) as well as fluid means can reduce and/or remedy imperfections of the gemstone in a simple and rapid manner.

Optionally, the fluid means remains at least partly and in particular completely in the gemstone after the solidification of a partial melting of the gemstone (thus after a renewed solidification of a part-melt).

For example, a flow means for rubies includes or is borax.

Advantageously, a flow means which is applied in a processing step of the gemstone in any case can be used at least partly or completely as a carrier fluid. In this manner, the method for rendering the gemstone traceable can be combined at least partly with the steps of a processing of the gemstone, in particular of the firing. This saves costs, time, energy and material.

The carrier fluid optionally at least partly or completely remains in the gemstone after the transport of the marker to the placement location.

Optionally, the carrier fluid is at least partially or completely removed from the gemstone after the transport of the marker to the placement location.

Alternatively, the marker can also be transported to the placement location without any carrier fluid. For example, the marker can be blown in in powder form. A transport of the marker by way of electromagnetic fields and/or by way of ionising radiation is likewise conceivable—which is possible with as well as without carrier fluid.

Optionally, the marker is fastened in the placement location after the transport to the placement location, by way of the gemstone being partially melted and resolidifying. Herein, in particular a flow means is used.

Optionally, the marker which is already fastened in the placement location is additionally fastened in the gemstone by way of the gemstone being partially melted and resolidifying. Herein, in particular a flow means is used.

Optionally, the marker is fastened in the placement locations after the transport to the placement location, by way of a melt including material that is foreign to the gemstone solidifying in a region around the marker. In particular, the material that is foreign to the gemstone includes or is glass, for example lead glass.

Optionally, the marker that is already fastened in the placement location is additionally fastened in the gemstone by way of a melt including material that is foreign to the gemstone being fastened in a region around the marker. In particular, the material that is foreign to the gemstone includes or is glass, for example lead glass.

Optionally, the gemstone is at least partially immersed into the carrier fluid with the suspended marker, in order to transport the marker that is suspended in the carrier fluid to the placement location in the gemstone. In particular, the gemstone can be completely immersed in the carrier fluid.

An at least partial immersion of the gemstone into the carrier fluid permits a simple, inexpensive, efficient, energy-saving and rapid transport of the marker to the placement location. Given several markers, a uniform distribution of the markers can be achieved by way of the immersing.

In particular, the gemstone can be immersed at least partially in the carrier fluid over a time duration of several hours. Additionally, the gemstone and/or the carrier fluid can be brought into motion, thus for example shaken, exposed to sound (in particular with ultrasound), pivoted rotated or stirred.

Alternatively, the gemstone can also be sprayed with the carrier fluid. The carrier fluid can also be injected into the placement locations.

In particular, a transport of the marker to the placement location can be effected at a transport pressure that is different to the ambient pressure. What is mean by ambient pressure is an air pressure of the surroundings.

For example, the transport of the marker to the placement location can be effected under overpressure, thus a pressure greater than the ambient pressure. In this case, the transport pressure is an overpressure. Herein, the overpressure can be greater than the ambient pressure by a factor of at least 1.5. In particular, the overpressure is greater than the ambient pressure by at least a factor of 5. In particular, the overpressure is greater than the ambient pressure by at least a factor of 10.

For example, the transport of the marker to the placement location can be effected under a vacuum, thus a pressure lower than the ambient pressure. In this case, the transport pressure is a vacuum. Herein, the vacuum can be lower than the ambient pressure by a factor of at least 1.5. In particular, the vacuum is lower than the ambient pressure by at least a factor of 5. In particular, the vacuum is lower than the ambient pressure by at least a factor of 10.

For example, the transport pressure corresponds to a pressure in a transport pressure space that is separated from a surroundings and in which at least a part of the gemstone and the marker are located whilst the marker is transported to the placement location.

In particular, the complete gemstone and the marker are located in a transport pressure space that is separated from a surroundings and in which the transport the pressure prevails, whilst the marker is transported to the placement location.

For example, the transport pressure thus prevails in a pressure chamber that can then also be denoted as transport pressure space.

For example, the transport pressure only prevails in a transport pressure region that includes the marker and the placement location, wherein the transport pressure region is designed as part of the surroundings.

Said differently, the transport pressure region is designed free of a separation from a surroundings. At least a part of the gemstone and the marker are located in this transport pressure region whilst the marker is transported to the placement location. For example, a transport pressure region in an environment around the placement locations, in which region the marker is transported to the placement location, can be provided by way of a targeted alignment of a fluid jet onto and/or around the gemstone.

Optionally, the marker is suspended in a carrier fluid that includes isopropanol. In particular, the marker is suspended in a carrier fluid that includes at least a 50% by weight of isopropanol.

Isopropanol is inexpensive. Isopropanol has good transport characteristics such as creep behaviour and surface wetting, for the transport of the marker into spatially limited and difficultly reachable placement locations. Isopropanol is not toxic and is simple in application. Isopropanol evaporates and vapourises rapidly and without residue.

Alternatively, a carrier fluid free of isopropanol can also be used. For example, an ethanol-based carrier fluid can be used.

In particular, the carrier fluid is evaporated or vapourised after the marker has been transported into the placement location.

Optionally, an additive is added to the carrier fluid before fastening the marker in the placement location of the gemstone, wherein the additive in particular is a primer.

An additive in the carrier fluid can play an assisting or even a major role on fastening the marker. A primer is a substance that adheres well to the gemstone and well as to the marker. A primer is referred to as a bonding agent. Expressed differently, a primer creates a close physical or chemical bonding in the boundary surface between the marker and the gemstone.

Alternatively, the carrier fluid can also be free of an additive. The carrier fluid can be free of a primer.

Optionally, the additive of the carrier fluid includes silicon.

Optionally, the additive of the carrier fluid includes silane and/or starting materials, from which silane can arise.

Optionally, a surface coating at least of a part-surface of the placement location forms before and/or on evaporation or vaporisation of the carrier fluid. The marker is fastened in the placement location of the gemstone by way of this surface coating. In particular, the surface coating includes silicon. In particular, the surface coating includes a silicate layer.

The marker can be fastened at the placement location in a stable and secure manner by way of the formation of a surface coating (at least on a part of the surface) of the placement location. The surface coating can be formed by the additive (for example by way of the adhesion of additive particles) and/or from a material that arises by way of the additive (for example, the additive can be a basis for a development of a surface coating, such as a liquid with respective starting materials). For example, the carrier fluid itself can form a surface coating on evaporation or vapourisation.

Optionally, the marker that is already fastened in the placement location is additionally fastened in the gemstone by way of a surface coating being formed at least on a part of the surface of the placement location.

For example, the fastening of the marker in the placement location can be effected by way of the solidifying of a substance on the basis of a chemical reaction of one or more components. The chemical reaction for solidifying the substance can be produced with or without an irradiation of the substance, in particular with or without irradiation by UV light. The solidifying of the substance on account of the chemical reaction can form a surface coating at least of a part of the surface of the placement location. Alternatively, the fastening of the substance on account of the chemical reaction can fasten the marker in the placement location, wherein the surface of the placement location remains free of a partial or complete surface coating.

Optionally, the marker that is already fastened in the placement location is additionally fastened in the gemstone by way of the solidifying of a substance being effected on account of a chemical reaction of one or more components.

Optionally, a surface of the marker is treated before the fastening of the marker in the placement location of the gemstone.

Herein, the point in time of the treatment of the surface of the marker lies at or after a beginning of the method for rendering traceable, thus at a point in time after the creation of the marker. In particular, the manufacture of the marker does not belong to the method of rendering traceable. In particular, the surface of the marker is treated before the suspending in the carrier fluid. In particular, the surface of the marker is treated in the carrier fluid.

The fastening of the marker can be effected in a simple, stable and/or permanent manner by way of a treatment of the surface of the marker. The fastening of the marker can be simplified by a treated surface. The treating of the surface can mean, for example, that the chemical and/or physical surface nature is changed, and/or for example that the marker obtains an electrical charge. In particular, a negative electrical charge is conceivable. A magnetisation of the marker can also be carried out. The surface of the marker however can also remain untreated before the fastening in the placement location.

The marker is optionally designed essentially as particles.

What is meant by particles are tiny parts, thus small solid bodies. For example, particles are solid constituents of aerosols, suspensions or powders.

A marker is designed essentially as a particle if at least 70% of its volume is a particle. In particular, a marker is designed essentially as a particle if at least 80% of its volume is a particle. In particular, a marker is designed essentially as a particle if at least 90% of its volume is a particle.

The marker is optionally designed in an essentially spherical manner. In particular, the marker is designed in an encapsulated manner.

A marker is designed essentially spherically if, in the radial direction of the marker, the smallest radius from the mass middle point of the marker is maximally 10% smaller than the largest radius. In particular, a marker is designed essentially spherically if the smallest radius is maximally 20% smaller than the largest radius. In particular, a marker is designed essentially spherically if the smallest radius is maximally 30% smaller than the largest radius.

The marker can also be designed in a cuboid-shaped, cylinder-shaped, n-polygon-shaped, tetrahedral, conical or ellipsoidal manner. The marker can also have an irregular shape. For example, the marker in regions can combine different ones of the aforementioned shapes.

A marker is designed in an encapsulated manner if the marker is designed as a container with a content.

Optionally, the marker has a size of 10 nm to and of 1000 nm. In particular, the marker has a size of 10 nm to and of 500 nm, in particular of 20 nm to and of 200 nm.

The size of the marker is to be understood as a maximal extension of that dimension, in which the marker is largest.

Optionally, the marker has an electrical charge. In particular, the marker has a negative electrical charge.

An electrical charge of the marker (independently of whether the charge originates from a surface treatment of the marker or arises in another manner) can help with the fastening of the marker in the placement location.

Alternatively, the marker is electrically neutral.

Optionally, the marker includes DNA, wherein the marker is unambiguously identifiable by way of the DNA.

Optionally, the DNA is manufactured artificially for the purpose of the traceability.

In this case, the DNA is thus a carrier of the characterising characteristic, on the basis of which the marker is unambiguously identifiable. Expressed differently, the characterising characteristic of the marker is designed in the form of DNA which is encompassed by the marker. The DNA can be identified on the basis of the information which is stored therein and can be differentiated from other DNA.

The acquisition of the marking information can optionally be effected by way of storing the marker information in a digital logbook.

The rendering traceable of the gemstone can be effected, assisted and/or supplemented by a digital form of a logbook. A digital logbook is to be understood as digital technology that permits the marking information—for example also including the transfer or the processing of a gemstone—to be acquired, stored and represented. The acquisition date as well as possibly also the precise acquisition time can additionally be logged for each marking information. This digital type of time logging can also be called hashtag. The hashtag can also be described as a digital time punch for each entry. By way of the repeated acquisition of marking information, in particular in combination with a hashtag, not only can the marking information be rendered traceable at the point in time of the marking, but also the marking information of subsequent steps of the gemstone in its trading process. These for example can be further processing processes, laboratory assessments, jeweller's work and trade activities. The digital logbook and herewith the marking information that is acquired therein can be stored and/or made accessible in a data network, for example in the internet on central and/or decentral data memories.

The gemstone can be identified before an entry into the digital logbook. In particular, a marker that is already previously fastened on the gemstone can be used for this. If a marker that is already fastened on the gemstone is identified (and on account of this also the gemstone), then this marker can be used further for the next marking information of this gemstone.

Alternatively or additionally, also individual or several other features of the gemstone can be used for the identification, such as, for example, optical, physical and/or chemical characteristics. These other features, for example, can be the dimensions, the weight, microscopic and/or macroscopic inner features and/or the colour.

If the repeated acquisition of marking information concerning the same gemstone (verified by the unambiguous identification of the gemstone before the acquisition of the next marking information) is stored in a manipulation-proof manner, then a complete series of steps in its trading and processing chain can be rendered traceable with a single marker (or with a single variety of marker). In other words, by way of an unambiguous identification of the gemstone before the acquisition of the next marking information, a complete history of a specific gemstone can be acquired in a traceable manner using a single marker (or a single variety of marker). Expressed differently, a new marker or a new variety of marker is not necessary (but possible) for each new traceable event or each acquisition of marking information. In particular, the repeated acquisition of marking information concerning the same gemstone in a digital logbook can be designed in a manipulation-proof manner.

The access to the digital logbook can be made possible by way of different technologies. For example, these can be software programs and/or online applications (e.g. input via a homepage or webapp). For example, programs for mobile communication devices (smartphones or similar devices) with an internet access can also be optimised and made available (apps).

The acquisition of the marking information is optionally effected by way of using blockchain technology.

The acquisition of the marking information can also be achieved by way of the use of blockchain technology. Blockchain technology is herein used in order to realise the digital logbook. For example, this is achieved by way of decentrally constructed digital technology, which can be denoted as distributed (digital) ledger or distributed blockchain technology.

Blockchain technology permits a manipulation-proof, cheap and trustworthy management of a digital logbook.

A second aspect of this invention is a method for tracing a gemstone, including the method for rendering a gemstone traceable as described above, as well as the subsequent steps:

identifying the marker, tracing the gemstone by way of comparing the identified marker with the acquired marking information.

The gemstone is prepared with the help of the method for rendering the gemstone traceable as is described above, in order to permit the tracing. The tracing is carried out via the identifying of the marker and the comparing of the identified marker with the acquired marking information. The advantages and the significance of the tracing of gemstones have already been described further above.

A third aspect of the invention is a gemstone including a marker, wherein the marker is arranged and fastened in a placement location of the gemstone by way of the method for rendering the gemstone traceable as is described above.

Such a gemstone with a marker can be traced. The respective advantages have already been described further above.

BRIEF DESCRIPTION OF THE DRAWINGS

The subject-matter of the invention is hereinafter explained in more detail by way of preferred embodiment examples, which are represented in the accompanying drawings. In each case shown schematically are.

DETAILED DESCRIPTION OF THE INVENTION

Figure 1A:
FIGS. 1a-1c a method for rending a gemstone traceable.

Basically, the same parts are provided with the same reference numerals in the figures.

Figure 1B:
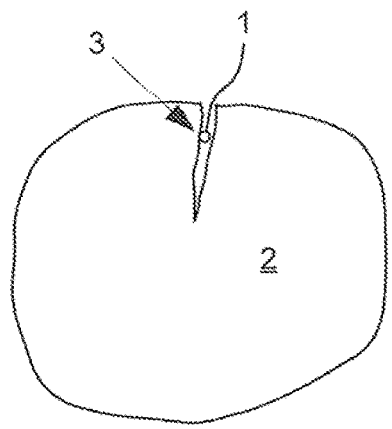
Figure 1C:
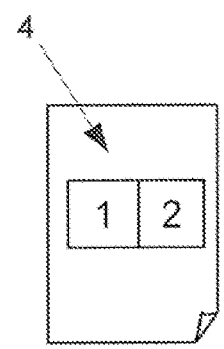

FIGS. 1a to 1c very schematically show a method for rendering a gemstone 2 traceable. Firstly, a marker 1 is provided, as is represented in FIG. 1a. The marker 1 in FIG. 1a is represented in a much enlarged manner; the marker 1 is not visible to the naked eye. The marker 1 is an essentially spherical particle with a diameter of 80 nm, thus a nanoparticle. The marker 1 includes DNA which is used for unambiguously identifying the marker 1. Apart from the DNA, the marker includes material that is based on silicon. The marker 1 in this embodiment is a type of marker as is described, for example, in the patent application publication WO2013143014A1.

A gemstone 2, which in the present example is an emerald, is represented in FIG. 1b. This gemstone 2 includes a placement location 3. In this example in FIG. 1b, the placement location 3 is represented enlarged and is formed as a micro-crack or also fissure in the gemstone 3. The marker 1 is fastened in this placement location 3 of the gemstone 3. As is represented in the FIG. 1c, marking information 4 is acquired, the marking information including the fact that the marker 1 has been fastened to the gemstone 2. The marking information 4 is typically stored in an electronic, available data bank that is protected from manipulation, unauthorised retrieval and/or data loss via suitable security measures.

A method for rendering a gemstone 2 traceable is represented very schematically in FIGS. 2a to 2f, wherein a carrier fluid 10 is used in order to transport the marker 1 to the placement location 3. The marker 1, the gemstone 2 with the placement location 3, as well as the marking information 4 are identical to those of FIGS. 1a to 1c. In the method that is represented in FIGS. 2a to 2f, several markers 1 (represented in FIG. 2a) are used. For this, the markers 1 are suspended in a carrier fluid 10, in this case isopropanol. The suspension of carrier fluid 10 and markers 1 is represented in a vessel 11 in FIG. 2b.

Figure 2A:
FIGS. 2a-2f a method for rendering a gemstone traceable amid the use of a carrier fluid.
Figure 2B:
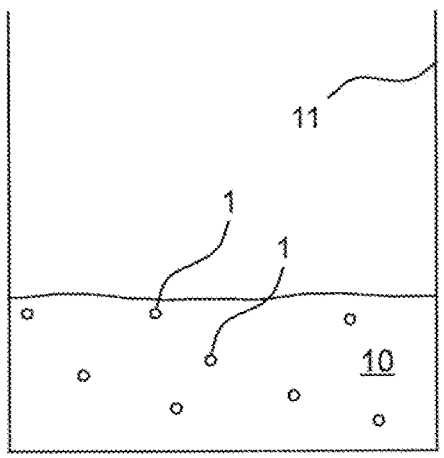
Figure 2C:
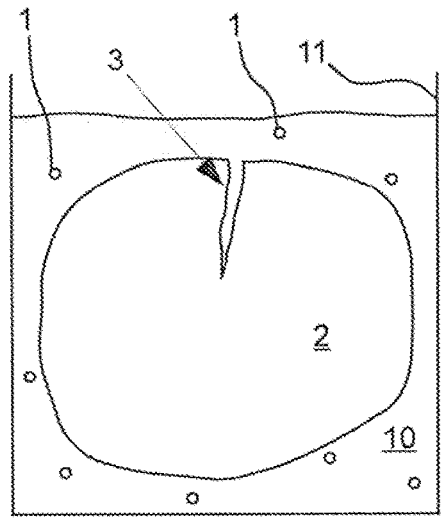
Figure 2D:
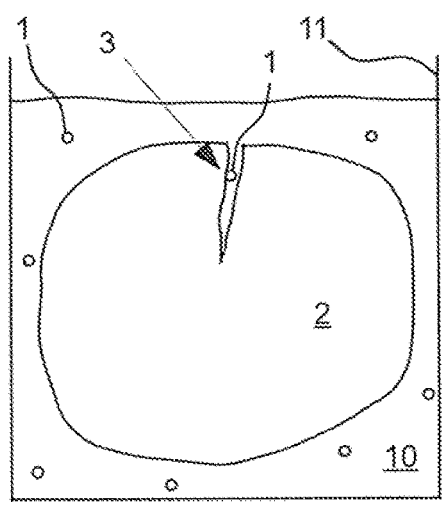

After suspending the marker 1 in the carrier fluid 10, the gemstone 2 is completely immersed in this suspension (see FIG. 2c). The complete vessel 11 is moved, more specifically is shaken at a frequency of 900 Hz at room temperature in a shaker whilst the gem 2 is submersed in the suspension. The shaking lasts for 4 hours. During this time, at least one marker 1 of the suspension is transported to the placement location 3 thanks to the carrier fluid 10, as is shown in FIG. 2c.

After the shaking of the vessel 11, the gemstone 2 is removed from the vessel 11, and the carrier fluid 10 can evaporate at room temperature. In this manner, the marker 1 is fastened in the placement location 3 of the gemstone 2. The acquisition of the marking information 4 is subsequently effected analogously to the method of FIGS. 1a to 1c.

Figure 2E:
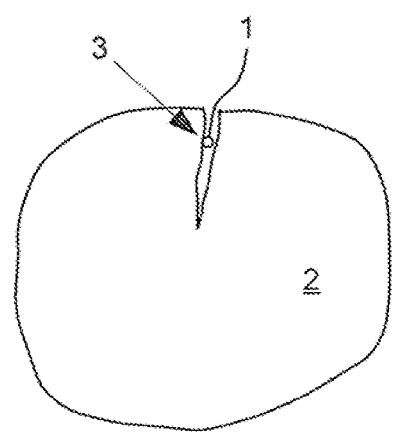
Figure 2F:
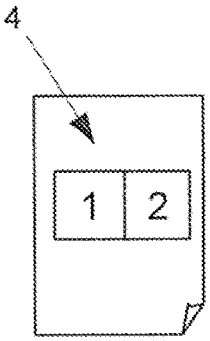
Figure 3A:
FIGS. 3a-3f a method for rendering a gemstone traceable amid the use of a carrier fluid and an additive.
Figure 3B:
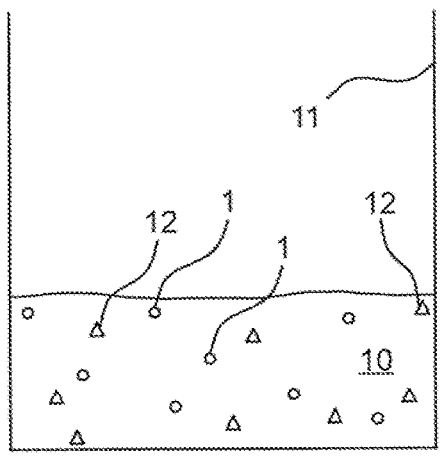
Figure 3C:
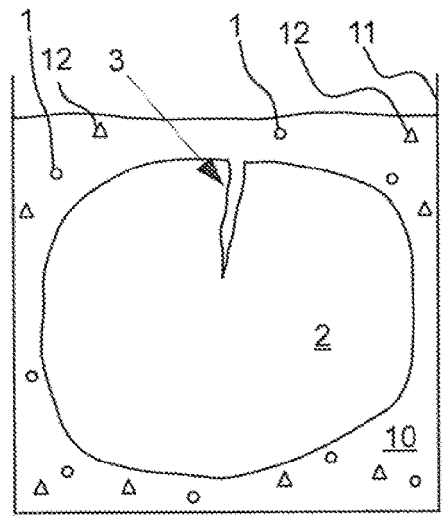
Figure 3D:
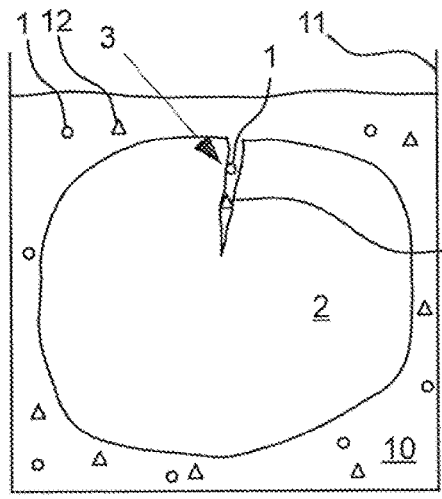

FIGS. 3a to 3f show a method that is analogous to the method in FIGS. 2a to 2f, with the difference that the suspension, apart from the carrier fluid 10 and the markers 1, yet also includes the additive 12. The additive 12 is represented in the FIGS. 3b to 3e as a triangular symbol. However, the additive 12 in the present case is not a particle, but consists of a fluid mixture of ammonia, tetraethyl orthosilicate and pure water. This additive 12 in the form of a fluid mixture serves as a basis for the formation of a silicate layer. Accordingly, the additive 12 is represented in suspension in the vessel 11 in FIG. 3b, and likewise in FIGS. 3c and 3d with the immersed gemstone 2. The additive 12 is also transported to the placement location 3 by the carrier fluid 10, as is shown in FIG. 3d.

Figure 3E:
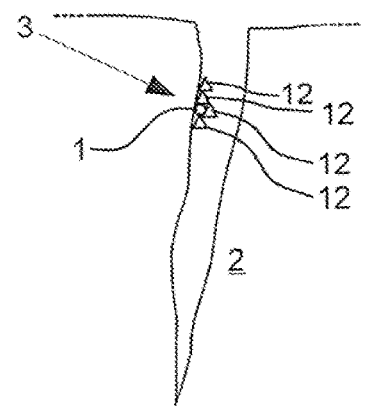
Figure 3F:
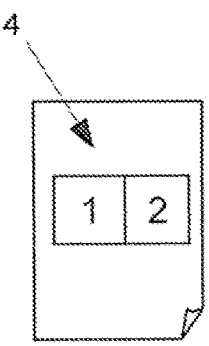

FIG. 3e schematically shows the placement location 3 of the gemstone 2 in a much enlarged manner. In FIG. 3e, the gemstone 2 has already been removed from the vessel 11, and the carrier fluid 10 has also already evaporated. On account of the additive 12, a surface coating has formed on a part of the surface of the placement location 3, represented by a rowing of triangular symbols of the additive 12. The marker 1 is fastened on the placement location 3 of the gemstone 2 by way of the surface coating.

The gemstones 2, which are marked with the different aforedescribed methods, are represented in FIGS. 1b, 2e and 3e (however only as a detail in 3e). These gemstones 2 thus include a marker 2. Together with the marking information 4, which is symbolically represented in FIGS. 1c, 2f and 3f, it is possible to trace these gemstones 2.

The method for tracing a gemstone 2 includes the steps of the method for rendering the gemstone traceable 2, said steps having been represented above. Thereafter, the gemstone 2 that is made traceable is examined, in order to identify the marker 1 that is fastened thereto. This is effected by way of releasing the DNA from the marker 1 that is located in the placement location 3 of the gemstone 2. Specifically, an etching solvent is applied, in order to at least partly dissolve the marker 1 and by way of this to release the DNA. The DNA is thereupon identified by way of qPCR (quantitative real-time PCR—a method based on a polymerase chain reaction for duplicating the DNA as well as a subsequent fluorescence measurement for quantifying the DNA). The marker 1 is identified in this manner. By way of using the marking information 4 and a corresponding comparison, one may draw conclusions concerning the corresponding gemstone 2 by way of identifying the marker 1 and by way of the information that concerns the marker 1 and that is encompassed by the marking information 4. The gemstone 2 is hence likewise identified by the information that is encompassed by the marking information 4, and the method for tracing is completed—since the gemstone 2 has been traced back to the event of the gemstone 2 having been marked with the marker 1. Inasmuch as the marking information 4 has been accordingly acquired, the location and the point in time of the application of the method for rendering traceable can be inferred, and/or further information such as for instance the origin from a mine or the like (as already described above).

The invention claimed is:

1. A method for rendering a gemstone traceable, comprising the steps:
   providing an invisible marker, wherein the marker is unambiguously identifiable,
   fastening the marker in a placement location of the gemstone, and
   acquiring marking information which includes that this unambiguously identifiable marker is fastened to the gemstone;
   wherein the marker, suspended in a carrier fluid comprising at least 50% by weight of isopropanol, is transported to the placement location, in order to fasten the marker in the placement location of the gemstone.

2. The method according to claim 1, wherein the gemstone is immersed at least partly into the carrier fluid with the suspend marker, in order to transport the marker, which is suspended in the carrier fluid, to the placement location of the gemstone.

3. The method according to claim 1, wherein an additive is added to the carrier fluid before the fastening of the marker in the placement location of the gemstone, wherein the additive is a primer.

4. The method according to claim 3, wherein the additive comprises silicon.

5. The method according to claim 3, wherein a surface coating of at least a part-surface of the placement location forms before and/or on evaporating or vapourising the carrier fluid, by way of which surface coating the marker is fastened in the placement location of the gemstone, wherein the surface coating comprises silicon.

6. The method according to claim 1, wherein a surface of the marker is treated before the fastening of the marker in the placement location of the gemstone.

7. The method according to claim 1, wherein the marker is designed as a particle.

8. The method according to claim 1, wherein the marker is designed in an essentially spherical manner and in an encapsulated manner.

9. The method according to claim 1, wherein the marker has a size of between about 10 nm to 1000 nm.

10. The method according to claim 9, wherein the marker has a size of between about 10 nm to 500 nm.

11. The method according to claim 10, wherein the marker has a size of between about 20 nm to 200 nm.

12. The method according to claim 1, wherein the marker comprises an electrical charge.

13. The method according to claim 1, wherein the marker comprises DNA, and wherein the marker is unambiguously identifiable by the DNA.

14. A method for tracing a gemstone, comprising the method for rendering a gemstone traceable according to claim 1, as well as the subsequent steps of:
   identifying the marker,
   tracing the gemstone by way of comparing the identified marker with the acquired marking information.

15. A gemstone comprising a marker, wherein the marker is arranged and fastened in a placement location of the gemstone by way of the method for rendering the gemstone traceable according to claim 1.

* * * * *